(12) United States Patent
Murdeshwar

(10) Patent No.: US 11,007,078 B2
(45) Date of Patent: May 18, 2021

(54) DEVICE AND METHOD FOR SENSING PERFORATION OF UTERINE TISSUE

(71) Applicant: Gyrus ACMI, Inc., Southborough, MA (US)

(72) Inventor: Nikhil Murdeshwar, Maple Grove, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 348 days.

(21) Appl. No.: 15/924,659

(22) Filed: Mar. 19, 2018

(65) Prior Publication Data

US 2019/0282397 A1    Sep. 19, 2019

(51) Int. Cl.
*A61F 7/12* (2006.01)
*A61B 5/01* (2006.01)
*A61B 5/00* (2006.01)
*A61B 18/02* (2006.01)
*A61B 18/00* (2006.01)

(52) U.S. Cl.
CPC ............... *A61F 7/123* (2013.01); *A61B 5/01* (2013.01); *A61B 18/02* (2013.01); *A61B 5/4318* (2013.01); *A61B 5/4325* (2013.01); *A61B 5/4331* (2013.01); *A61B 5/4337* (2013.01); *A61B 2018/00017* (2013.01); *A61B 2018/0022* (2013.01); *A61B 2018/00559* (2013.01); *A61B 2018/00791* (2013.01); *A61B 2018/0212* (2013.01); *A61B 2018/0262* (2013.01); *A61B 2562/0271* (2013.01)

(58) Field of Classification Search
CPC ......... A61F 7/123; A61B 5/01; A61B 5/4318; A61B 5/4325; A61B 5/4331; A61B 5/4337; A61B 2017/00084; A61B 2018/00714; A61B 2018/00791; A61B 2018/00797; A61B 2018/00559; A61B 2562/0271
See application file for complete search history.

(56) References Cited

U.S. PATENT DOCUMENTS

| | | | |
|---|---|---|---|
| 8,197,470 B2 * | 6/2012 | Sharkey | ................. A61B 18/04 606/21 |
| 8,998,901 B2 | 4/2015 | Truckai et al. | |
| 9,050,102 B2 | 6/2015 | Truckai | |
| 9,788,890 B2 | 10/2017 | Toth et al. | |
| 2004/0122327 A1 * | 6/2004 | Belson | ............... A61B 1/00082 600/476 |
| 2015/0335380 A1 * | 11/2015 | Chee | ...................... A61B 18/04 606/34 |

\* cited by examiner

*Primary Examiner* — Devin B Henson
(74) *Attorney, Agent, or Firm* — Schwegman Lundberg & Woessner, P.A.

(57) ABSTRACT

An apparatus includes a shaft having a proximal end and a distal end; a stem extending from the distal end of the shaft and comprising a first cover and a second cover, the first cover and the second cover being configured to inhibit access to fallopian tubes of a patient; and a plurality of temperature sensors disposed on the shaft and on the stem. At least one of the temperature sensors is positioned between the proximal end of the shaft and the distal end of the shaft and at least one of the temperature sensors is positioned on the stem.

20 Claims, 5 Drawing Sheets

DEVICE AND METHOD FOR SENSING PERFORATION OF UTERINE TISSUE

BACKGROUND

Field of the Invention

The exemplary and non-limiting embodiments described herein relate generally to devices and methods that relate to procedures involving uterine tissue. The exemplary and non-limiting embodiments described herein relate more particularly to devices and surgical procedures pertaining to the sensing of perforations in a uterus.

Brief Description of Prior Developments

Surgical techniques are often performed to address problems with uterine tissue. One surgical technique may involve endometrial ablation to address abnormal uterine bleeding, such as menorrhagia. In ablation procedures, the endometrial layers at the inner uterine wall are removed or destroyed such that the opposing walls of the myometrium collapse onto each other and the tissue contracts and develops into a scar. Any endometrium remaining after the ablation is trapped beneath the scar, thus preventing further bleeding.

Some ablation procedures heat or freeze uterine tissue utilizing technologies involving, for example, the application of radio frequency (RF) energy to activate argon plasma, cryogenics, thermal energy, or steam. One example is the use of a gaseous medium, such as nitrous oxide, which is released through a nozzle into a uterine conformal balloon at the distal end of the nozzle, to treat the uterine tissue at cryogenic temperatures.

Before undertaking a surgical procedure such as ablation, uterine integrity is determined. Methods of determining uterine integrity generally involve inflating the uterus with carbon dioxide and checking for a pressure drop over a specified period of time. An excessive pressure drop during this time period would likely indicate a perforation in the uterus. After confirming uterine integrity, an ablation (or other uterine treatment) may be carried out.

SUMMARY

In accordance with one aspect of the invention, an apparatus comprises: a shaft having a proximal end and a distal end; a stem extending from the distal end of the shaft and comprising a first cover and a second cover, the first cover and the second cover being configured to inhibit access to fallopian tubes of a patient; and a plurality of temperature sensors disposed on the shaft and on the stem. At least one of the temperature sensors is positioned between the proximal end of the shaft and the distal end of the shaft and at least one of the temperature sensors is positioned on the stem.

In accordance with another aspect of the invention, a medical device comprises: a hollow shaft having a proximal end and a distal end; a seal on the hollow shaft between the proximal end and the distal end; a stem extending from the distal end of the hollow shaft, the stem comprising a first cover configured to inhibit access to a first fallopian tube of a patient and a second cover configured to inhibit access to a second fallopian tube of the patient; and a plurality of temperature sensors disposed along a length of the shaft and the stem. A first of the temperature sensors is positioned between the proximal end of the shaft and the seal, a second of the temperature sensors is positioned forward of the first of the temperature sensors and aft of the seal, and a third of the temperature sensors is positioned on the stem.

In accordance with another aspect of the invention, a method comprises: providing a medical device having a hollow shaft having a proximal end and a distal end, a seal on the hollow shaft between the proximal end and the distal end, a stem extending from the distal end of the hollow shaft, the stem comprising a first cover configured to inhibit access to a first fallopian tube of a patient and a second cover configured to inhibit access to a second fallopian tube of the patient, and a plurality of temperature sensors disposed along a length of the shaft and the stem; inserting the medical device into a uterine cavity of the patient; inhibiting access to the first fallopian tube and the second fallopian tube using the first cover and the second cover; sealing the uterine cavity in a cervical canal of the patient; inflating the uterine cavity; measuring temperatures using the plurality of temperature sensors; and ascertaining a structural integrity of the uterine cavity based on the measured temperatures. The structural integrity is determined during a medical procedure.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
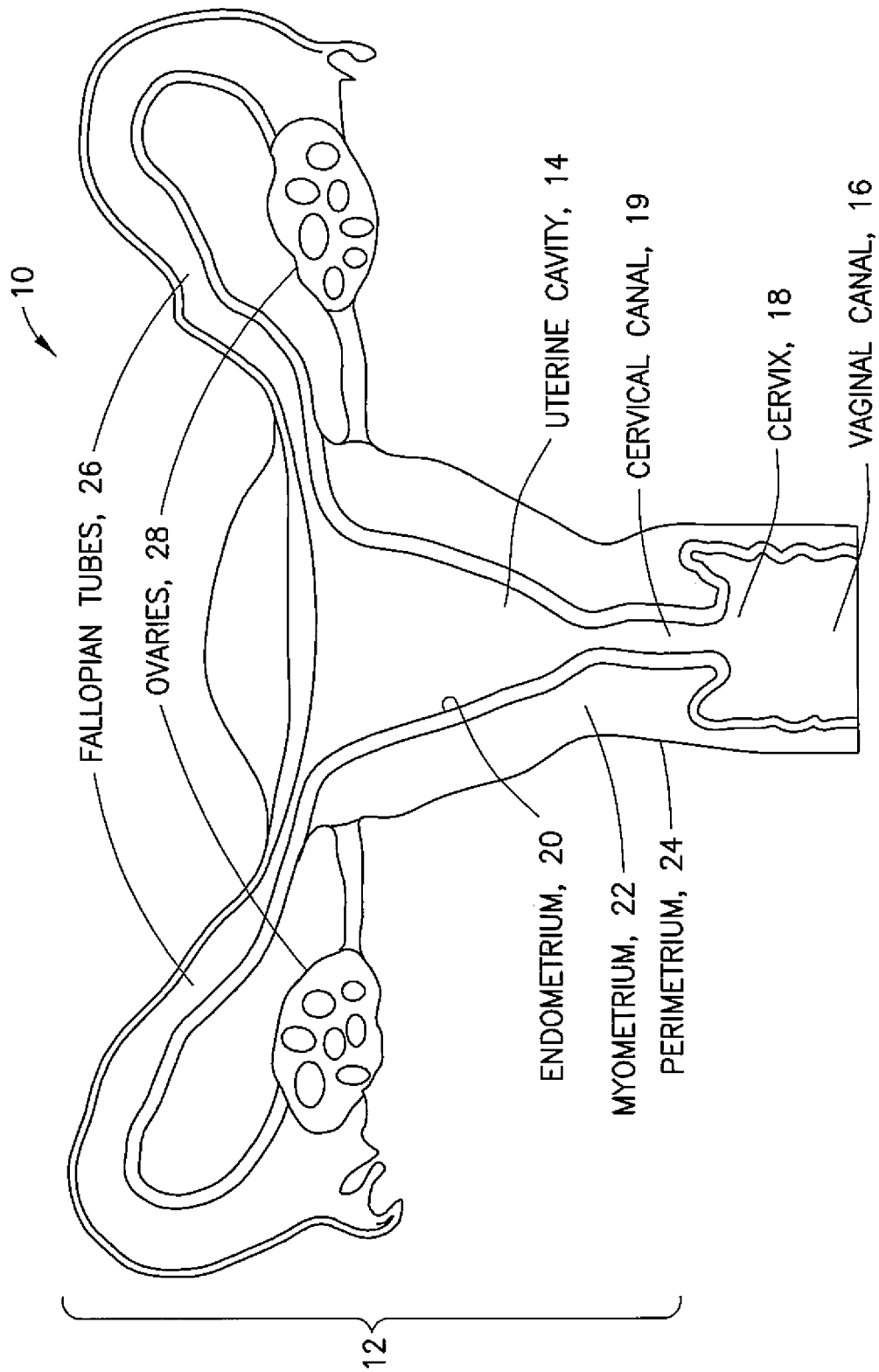
FIG. 1 is a schematic representation of a uterus.

Referring to FIG. 1, a gynecological cavity is shown and designated generally by the reference number 10. The gynecological cavity 10 includes the uterus 12 defining the uterine cavity 14, access to which is generally through the vaginal canal 16, the cervix 18, and the cervical canal 19. The uterine cavity 14 is lined with the endometrium 20, which is a mucous membrane lining the inner uterine wall and which thickens during the menstrual cycle in preparation for possible implantation of an embryo. The endometrium 20 is supported by the myometrium 22 (middle uterine wall). The perimetrium 24 (outer uterine layer) is located on the outer surface of the myometrium 22. The fallopian tubes 26 extend from an upper portion of the uterus 12 and terminate in fimbriated and funnel-shaped openings that wrap partway around the ovaries 28.

Figure 2A:
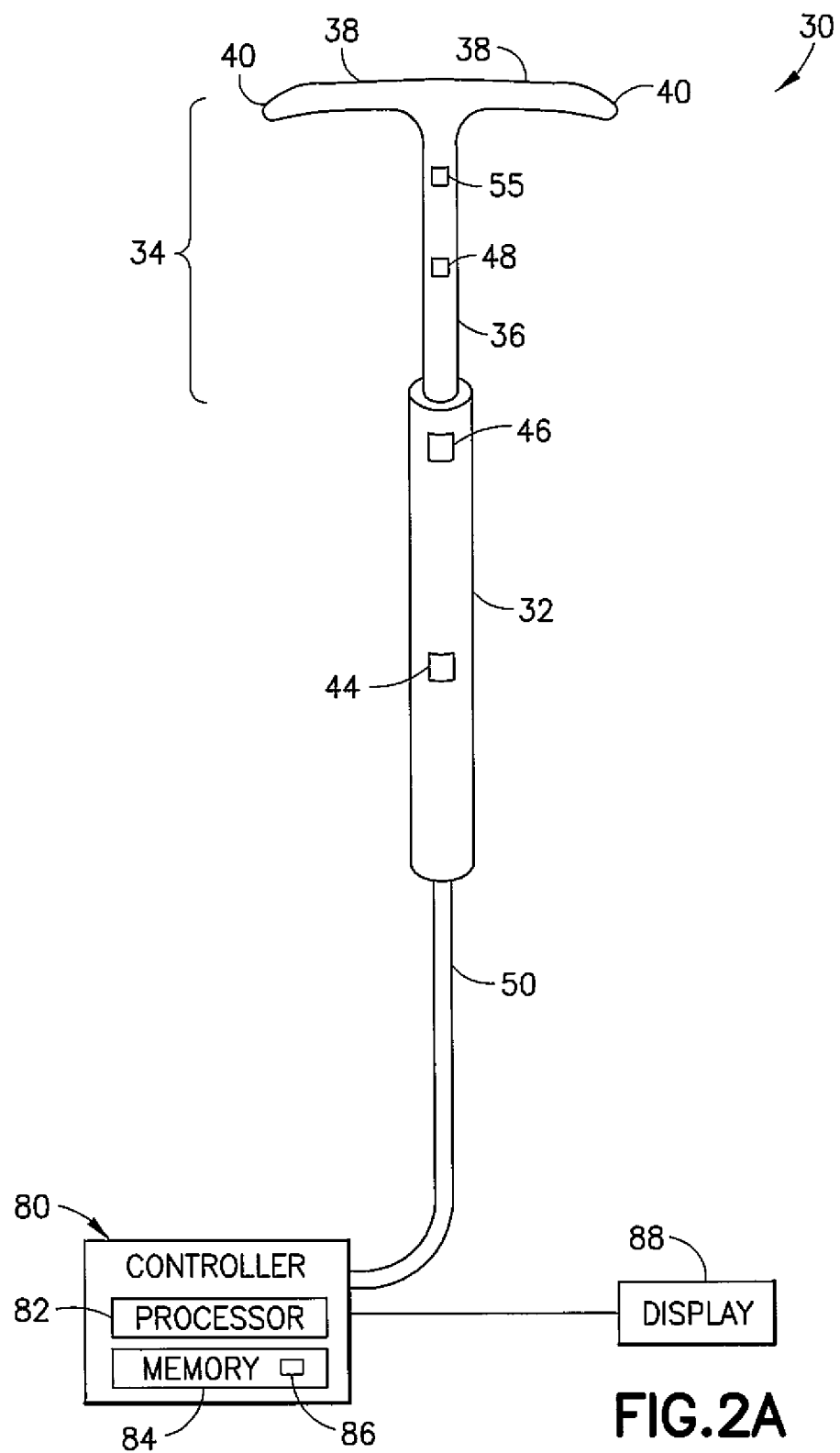
FIG. 2A is a schematic representation of one embodiment of a medical device for determining uterine integrity.
Figure 2B:
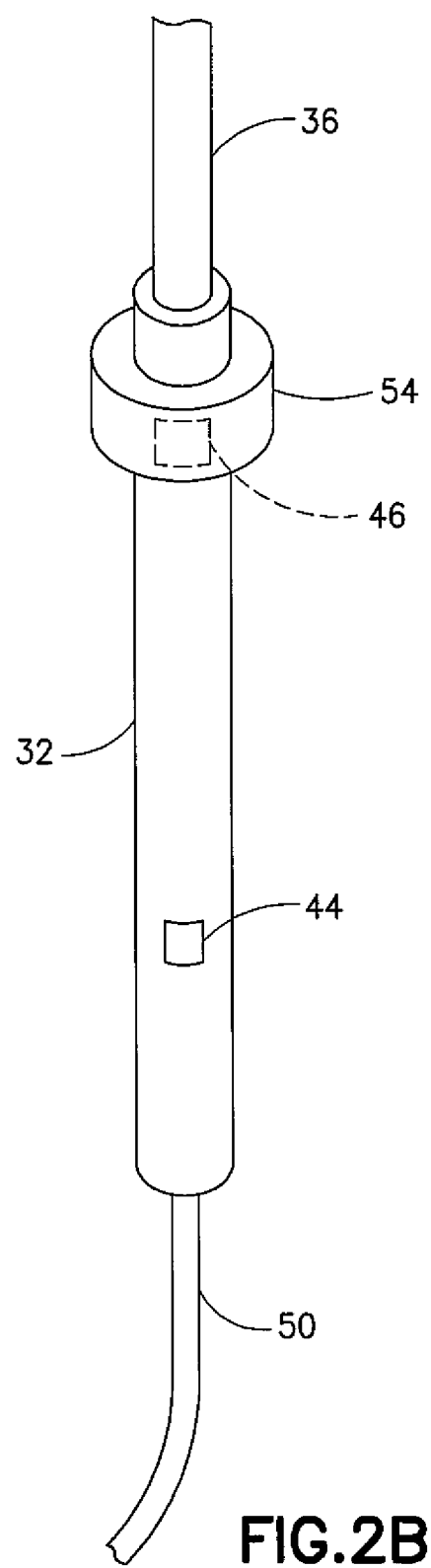
FIG. 2B is a schematic representation of another embodiment of a medical device for determining uterine integrity.

Referring to FIG. 2A, a medical device for confirming uterine integrity during treatment of the uterus 12 is designated generally by the reference number 30 and is hereinafter referred to as "device 30." Device 30 comprises a shaft 32 having a proximal end at which a user (for example, a surgeon or other medical professional) controls the device 30 and further having a distal end at which a stem 34 is operatively mounted to close off or at least inhibit access to the fallopian tubes 26. The shaft 32 may be hollow. An area proximate the distal end of the shaft 32 forms a seal in the cervical canal 19 when the device 30 is positioned in the uterine cavity 14.

The stem 34 is substantially T-shaped with a trunk 36 coaxial with and extending from the distal end of the shaft 32 and arms 38 extending at substantial right angles from the distal end of the trunk 36. Covers 40 are formed with or coupled to ends of the arms 38. Surfaces of the covers 40 are rounded and smoothed to form elements that facilitate temporary blockage of access to the fallopian tubes 26 and assist in providing for a substantially fluid-tight seal of the uterine cavity 14.

A plurality of temperature sensors is positioned along a length of the device 30. For example, a first sensor 44 may be positioned closer to the proximal end of the shaft 32, a second sensor 46 may positioned forward of the first sensor 44 but still on the shaft 32, and a third sensor 48 may be positioned on the trunk 36. A tube 50 may extend from the proximal end of the shaft 32 to provide electrical connections at the temperature sensors 44, 46, 48, thus obviating the need for balloons and additional gas flow channels. This permits thin shaft designs that are easily, and more comfortably, inserted into the uterus 12 through the cervical os. Simplicity and ease of use of the device 30 provide for a low cost and efficient manner of confirming uterine integrity during a medical procedure such as an ablation.

Optionally, a complementary metal oxide semiconductor (CMOS) chip 55 may also be incorporated into the stem 34, along with a video imaging apparatus or suitable video imaging componentry (such as a camera or the like), to allow the user of the device 30 to monitor operations within the uterine cavity 14. Allowing the user to monitor operations within the uterine cavity 14 includes, but is not limited to, allowing the user to monitor an ablation or other procedure.

The electrical connections at the temperature sensors 44, 46, 48 may extend through the tube 50 to a controller 80 having a processor 82 and a memory 84, the memory 84 including software 86. The controller 80 may be coupled to a display 88 to output imaging obtained from the video componentry on the CMOS chip 55 and/or to output the temperatures sensed at the temperature sensors 44, 46, 48 to the display 88.

Referring now to FIG. 23, the device 30 may include an inflatable annular member 54 positioned proximate the distal end of the shaft 32. Upon inflation of the inflatable annular member 54 with a suitable fluid, a resulting expansion thereof causes the formation of the seal in the cervical canal 19. The second sensor 46 may be positioned on the shaft 32 under the inflatable annular member 54, as shown, or it may be positioned proximate the inflatable annular member 54 toward the proximal end of the shaft 32.

Figure 3:
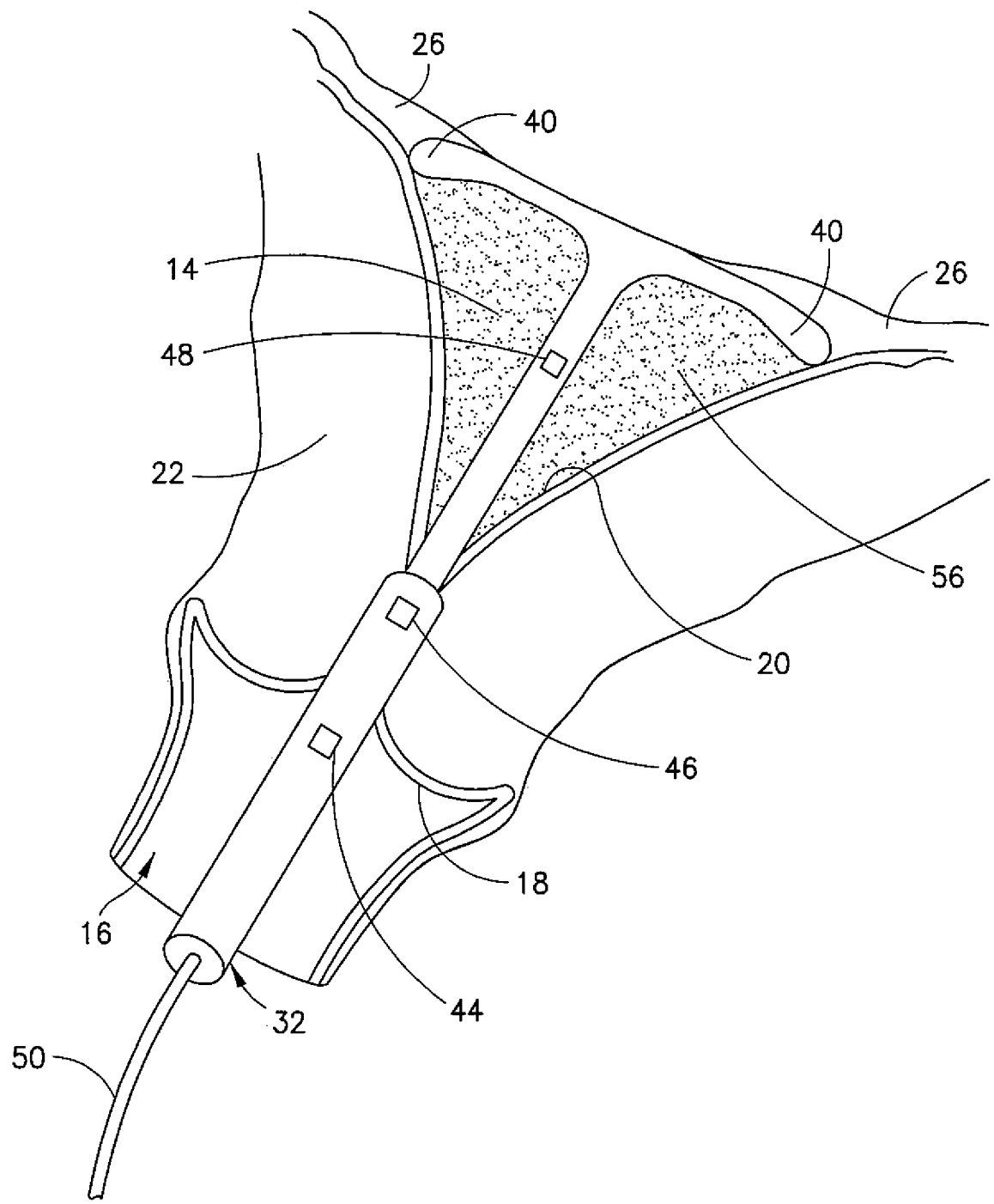
FIG. 3 is a schematic representation of the medical device of FIG. 2A in a uterus.

Referring now to FIG. 3, the device 30 may be inserted into a uterine cavity 14 in a manner similar to that of an intrauterine device (IUD) and is used in conjunction with a gaseous medium 56 (such as a nitrous oxide or carbon dioxide) introduced into the uterine cavity 14 through a first conduit extending through the shaft 32 to the distal end thereof. A second conduit may be positioned proximal to the first conduit to provide an exhaust channel for the introduced gaseous medium 56 (for example, using suction). As shown, once the device 30 is inserted into the patient, pressure in the uterine cavity 14 resulting from the introduced gaseous medium 56 causes the covers 40 to block the flow of the gaseous medium 56 into the fallopian tubes 26. Then, the first sensor 44 measures vaginal temperature, for example, temperature proximate the external os of the cervix 18, the second sensor 46 measures temperature in the cervical canal 19 at the portion of the shaft 32 forming the seal, and the third sensor 48 measures the temperature within the uterine cavity 14. During a medical procedure in which the device 30 is used, the temperatures at the three locations indicated by the first sensor 44, the second sensor 46, and the third sensor 48 will be in equilibrium. In the event of a perforation in a wall of the uterus 12, instability in the temperature readings will alert the user.

Figure 4:
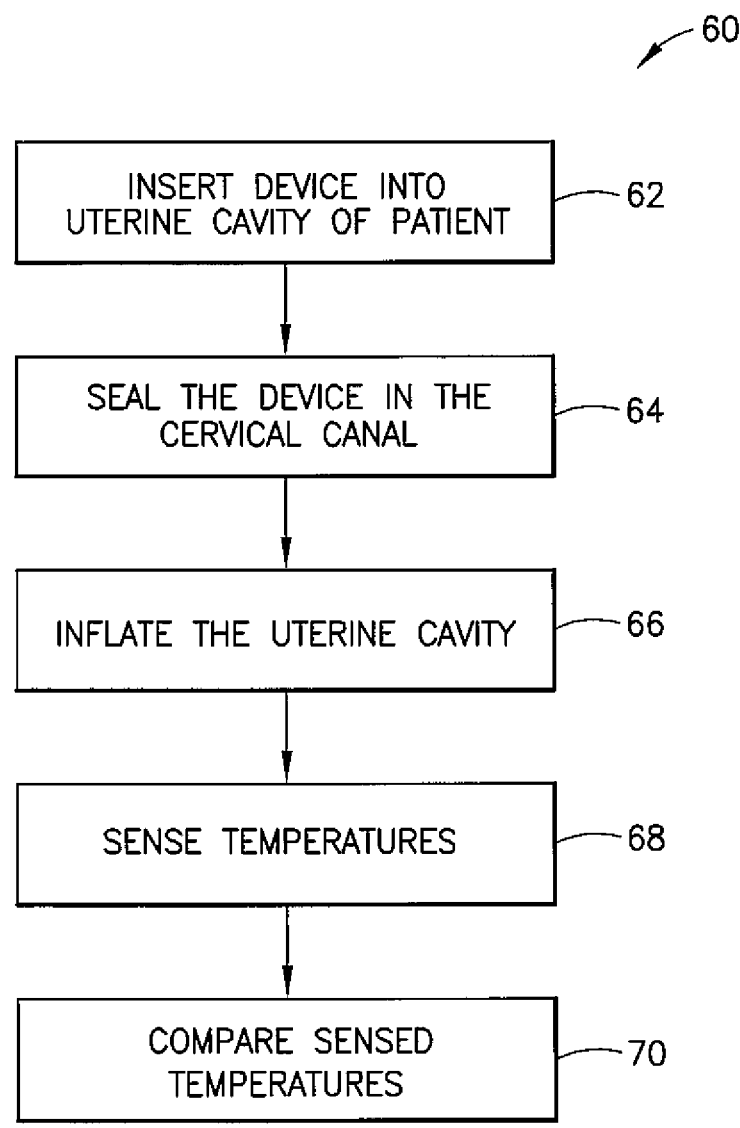
FIG. 4 is a flow of one exemplary embodiment of a method of using a medical device for determining uterine integrity by sensing and comparing temperatures at various places in a uterus and in a vaginal canal.

Referring now to FIG. 4, a flow of one exemplary method of using the device 30 is shown generally at 60 and is hereinafter referred to as "method 60." In method 60, the device 30 may be inserted into the uterine cavity 14 of a patient, as indicated at 62, and sealed in the cervical canal 19, as indicated at 64. The uterine cavity 14 may then be inflated, as indicated at 66, using a gaseous medium. As indicated at 68, the temperatures at various locations along the device 30 are sensed and possibly recorded. The sensed temperatures are then compared, as indicated at 70. If the sensed and compared temperatures at steady state vary by more than predetermined amounts, then the user may conclude that the structural integrity of the uterus 12 may be compromised (a wall of the uterine cavity 12 may be perforated).

The device 30 and use of the device 30 in the method 60 provides numerous advantages over the devices and methods previously employed. For example, using the device 30 and method 60, uterine integrity may be confirmed during treatment (rather than before) by sensing temperatures with any instability in the temperatures during treatment likely indicating a uterine perforation. Furthermore, the design of the device 30 is simplified by eliminating additional gas canisters, flow systems, and pressure gages. Additionally, the thin shaft design provides for easy insertion of the device 30 through the cervical os, thus reducing discomfort in the patient, helping to transition the methods described to outpatient office procedures, and facilitating the use of less potent pain blockers and anesthesia.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

In one aspect, an apparatus comprises: a shaft having a proximal end and a distal end; a stem extending from the distal end of the shaft and comprising a first cover and a second cover, the first cover and the second cover being configured to inhibit access to fallopian tubes of a patient; and a plurality of temperature sensors disposed on the shaft and on the stem. At least one of the temperature sensors is positioned between the proximal end of the shaft and the distal end of the shaft and at least one of the temperature sensors is positioned on the stem.

The stem may comprise a trunk and first and second arms extending from the trunk, end portions of each of the first and second arms defining the first cover and the second cover, respectively. The apparatus may further comprise a seal positioned proximate the distal end of the shaft. At least one of the temperature sensors may be positioned proximate the seal. The seal may comprise an inflatable annular member. The shaft may be hollow and may comprise electrical wiring coupling the plurality of temperature sensors to a controller. The controller may comprise a processor, a memory, and software configured to provide non-transitory signals pertaining to temperatures sensed by at least one of the temperature sensors. The apparatus may further comprise a video imaging apparatus disposed on the stem.

In another aspect, a medical device comprises: a hollow shaft having a proximal end and a distal end; a seal on the hollow shaft between the proximal end and the distal end; a stem extending from the distal end of the hollow shaft, the stem comprising a first cover configured to inhibit access to a first fallopian tube of a patient and a second cover configured to inhibit access to a second fallopian tube of the patient; and a plurality of temperature sensors disposed along a length of the shaft and the stem. A first of the temperature sensors is positioned between the proximal end of the shaft and the seal, a second of the temperature sensors is positioned forward of the first of the temperature sensors and aft of the seal, and a third of the temperature sensors is positioned on the stem.

When the medical device is inserted into a uterine cavity of the patient, the first of the temperature sensors may be configured to measure a vaginal temperature, the second of the temperature sensors may be configured to measure a temperature at a cervical canal of the patient, and the third of the temperature sensors may be configured to measure a uterine cavity temperature. The seal may comprise a member that is annularly inflatable about the shaft and positionable within a cervical canal of the patient. The temperature sensors of the plurality of temperature sensors may be electrically coupled to a controller through the hollow shaft. The controller may comprise a processor, a memory, and software configured to provide non-transitory signals pertaining to temperatures sensed by at least one of the temperature sensors. The medical device may further comprise a camera coupled to the stem and a display coupled to the controller, and the processor, the memory, and the software may be configured to provide non-transitory video signals from the camera to the display.

In another aspect, a method comprises: providing a medical device having a hollow shaft having a proximal end and a distal end, a seal on the hollow shaft between the proximal end and the distal end, a stem extending from the distal end of the hollow shaft, the stem comprising a first cover configured to inhibit access to a first fallopian tube of a patient and a second cover configured to inhibit access to a second fallopian tube of the patient, and a plurality of temperature sensors disposed along a length of the shaft and the stem; inserting the medical device into a uterine cavity of the patient; inhibiting access to the first fallopian tube and the second fallopian tube using the first cover and the second cover; sealing the uterine cavity in a cervical canal of the patient; inflating the uterine cavity; measuring temperatures using the plurality of temperature sensors; and ascertaining a structural integrity of the uterine cavity based on the measured temperatures. The structural integrity is determined during a medical procedure.

Inhibiting access to the first fallopian tube and the second fallopian tube may comprise blocking the first fallopian tube with the first cover and blocking the second fallopian tube with the second cover. Measuring temperatures using the plurality of temperature sensors may comprise measuring a vaginal temperature, measuring a temperature in the cervical canal, and measuring a temperature in the uterine cavity. Inflating the uterine cavity may comprise introducing carbon dioxide into the uterine cavity. Ascertaining a structural integrity of the uterine cavity based on the measured temperatures may comprise processing the measured temperatures using a controller having a processor, memory, and software. The method may further comprise monitoring at least one of the inserting, the inhibiting, the sealing, the inflating, and the measuring using a camera.

It should be understood that the foregoing description is only illustrative of the invention. Various alternatives and modifications can be devised by those skilled in the art without departing from the invention. Accordingly, the invention is intended to embrace all such alternatives, modifications, and variances which fall within the scope of the appended claims.

What is claimed is:

1. An apparatus, comprising:
a shaft having a proximal end and a distal end;
a stem extending from the distal end of the shaft and comprising a first cover and a second cover, the first cover and the second cover each having an outer surface configured to inhibit access to fallopian tubes of a patient; and
a plurality of temperature sensors disposed on the shaft and on the stem;
wherein at least one of the temperature sensors is positioned between the proximal end of the shaft and the distal end of the shaft and at least one of the temperature sensors is positioned on the stem; and
wherein the stem is substantially T-shaped and includes a trunk extending from the distal end of the shaft and first and second arms extending from a distal end of the trunk.

2. The apparatus of claim 1, wherein end portions of each of the first and second arms define the first cover and the second cover, respectively.

3. The apparatus of claim 1, further comprising a seal positioned proximate the distal end of the shaft.

4. The apparatus of claim 3, wherein at least one of the temperature sensors is positioned proximate the seal.

5. The apparatus of claim 3, wherein the seal comprises an inflatable annular member.

6. The apparatus of claim 1, wherein the shaft is hollow and comprises electrical wiring coupling the plurality of temperature sensors to a controller.

7. The apparatus of claim 6, wherein the controller comprises a processor, a memory, and software configured to provide non-transitory signals pertaining to temperatures sensed by at least one of the temperature sensors.

8. The apparatus of claim 1, further comprising a video imaging apparatus disposed on the stem.

9. A medical device, comprising:
a hollow shaft having a proximal end and a distal end;
a seal on the hollow shaft between the proximal end and the distal end;
a substantially T-shaped stem comprising a trunk extending from the distal end of the hollow shaft, a first arm extending substantially perpendicularly from a distal end of the trunk, a second arm extending substantially perpendicularly from the distal end of the trunk, a first cover disposed at an end of the first arm having an outer surface configured to inhibit access to a first fallopian tube of a patient, and a second cover disposed at an end of the second arm having an outer surface configured to inhibit access to a second fallopian tube of the patient; and
a plurality of temperature sensors disposed along a length of the shaft and the stem;
wherein a first of the temperature sensors is positioned between the proximal end of the shaft and the seal, a second of the temperature sensors is positioned forward of the first of the temperature sensors and aft of the seal, and a third of the temperature sensors is positioned on the stem.

10. The medical device of claim 9, wherein, when the medical device is inserted into a uterine cavity of the patient, the first of the temperature sensors is configured to measure a vaginal temperature, the second of the temperature sensors is configured to measure a temperature at a cervical canal of the patient, and the third of the temperature sensors is configured to measure a uterine cavity temperature.

11. The medical device of claim 9, wherein the seal comprises a member that is annularly inflatable about the shaft and positionable within a cervical canal of the patient.

12. The medical device of claim 9, wherein the temperature sensors of the plurality of temperature sensors are electrically coupled to a controller through the hollow shaft.

13. The medical device of claim 12, wherein the controller comprises a processor, a memory, and software configured to provide non-transitory signals pertaining to temperatures sensed by at least one of the temperature sensors.

14. The medical device of claim 13, further comprising a camera coupled to the stem and a display coupled to the controller, and wherein the processor, the memory, and the software are configured to provide non-transitory video signals from the camera to the display.

15. A method, comprising:
providing or obtaining a medical device having a hollow shaft having a proximal end and a distal end, a seal on the hollow shaft between the proximal end and the distal end, a substantially T-shaped stem comprising a trunk extending from the distal end of the hollow shaft, a first arm extending from a distal end of the trunk, a second arm extending from the distal end of the trunk, a first cover disposed at an end of the first arm having an outer surface configured to inhibit access to a first fallopian tube of a patient, a second cover disposed at an end of the second arm having an outer surface configured to inhibit access to a second fallopian tube of the patient, and a plurality of temperature sensors disposed along a length of the shaft and the stem;
inserting the medical device into a uterine cavity of the patient;
inhibiting access to the first fallopian tube and the second fallopian tube using the first cover and the second cover;
sealing the uterine cavity in a cervical canal of the patient;
inflating the uterine cavity;
measuring temperatures using the plurality of temperature sensors; and
ascertaining a structural integrity of the uterine cavity based on the measured temperatures;
wherein the structural integrity is determined during a medical procedure.

16. The method of claim 15, wherein inhibiting access to the first fallopian tube and the second fallopian tube comprises blocking the first fallopian tube with the first cover and blocking the second fallopian tube with the second cover.

17. The method of claim 15, wherein measuring temperatures using the plurality of temperature sensors comprises measuring a vaginal temperature, measuring a temperature in the cervical canal, and measuring a temperature in the uterine cavity.

18. The method of claim 15, wherein inflating the uterine cavity comprises introducing carbon dioxide into the uterine cavity.

19. The method of claim 15, wherein ascertaining a structural integrity of the uterine cavity based on the measured temperatures comprises processing the measured temperatures using a controller having a processor, memory, and software.

20. The method of claim 15, further comprising monitoring at least one of the inserting, the inhibiting, the sealing, the inflating, and the measuring using a camera.

* * * * *